United States Patent [19]
Hirsch

[11] Patent Number: 4,829,177
[45] Date of Patent: May 9, 1989

[54] POINT PROJECTION PHOTOELECTRON MICROSCOPE WITH HOLLOW NEEDLE

[76] Inventor: Gregory Hirsch, 365 Talbot Ave., #D8, Pacifica, Calif. 94044

[21] Appl. No.: 94,639

[22] Filed: Sep. 9, 1987

Related U.S. Application Data

[63] Continuation-in-part of Ser. No. 906,354, Sep. 11, 1986, abandoned.

[51] Int. Cl.$^4$ .............................................. G01N 23/00
[52] U.S. Cl. ................................... 250/306; 250/307; 250/423 P
[58] Field of Search ............... 250/305, 306, 307, 311, 250/327.2, 487, 423 P; 313/530

[56] References Cited

U.S. PATENT DOCUMENTS

| | | | |
|---|---|---|---|
| 3,796,901 | 3/1974 | Mayer et al. | 250/305 |
| 3,805,068 | 4/1974 | Lee | 250/306 |
| 3,864,572 | 2/1975 | vander Mast et al. | 250/306 |
| 3,896,308 | 7/1975 | Nemables et al. | 250/305 |
| 4,087,683 | 5/1978 | Lieb | 313/530 |
| 4,096,386 | 6/1978 | Rempfer et al. | 250/306 |
| 4,184,077 | 1/1980 | Washida | 250/483.1 |
| 4,215,274 | 7/1980 | Segall | 250/368 |
| 4,236,077 | 11/1980 | Sonoda et al. | 250/486.1 |
| 4,602,282 | 7/1986 | Kurano et al. | 358/107 |
| 4,624,835 | 11/1986 | Davis et al. | 250/306 |
| 4,680,635 | 7/1987 | Khurama | 358/106 |

OTHER PUBLICATIONS

Massey et al., "Subwavelength Resolution Far–Infrared Microscopy", *Applied Optics*, vol. 24, No. 10/15, May 1985.
"Soft X-Ray Microscopy of Biological Specimens", Kirz et al., *Synchrontron Radiation* published by Plenum Press of New York, N.Y. 1980, pp. 277–322.
Field Ion Microscopy published by American Elsevier, Muller et al., 1969.
Fishcer et al, "Submicroscopic Pattern Application with Visible Light", *J. Vac. Sci. Technol.*, 19(4), Nov./Dec. 1981.
Fischer et al., "Optical Characteristics of 0.1 μm Circular Apertures in a Metal Film as Light Sources for Scanning Ultramicroscopy", *J. Vac. Sci. Technol.*, B3(1)˙ Jan./Feb. 1985.
Fischer et al., "Near–Field Optical Scanning Microscopy and Enhanced Spectroscopy with Submicron Apertures", *Scanning Microscopy Supplement* 1, 1987 (pp. 47–52), Scanning Microscopy International, Chicago (AMF O'Hare), IL 60666 U.S.A.
Pohl et al., "Cal Stethoscopy: Image Recording with Resolution λ/20", *Appl. Phys. Lett.*, 44 (7), Apr. 1, 1984.
Fischer et al., "Near–Field Optical Scanning Microscopy in Reflection", *Appl. Phys. Letter*, 52(4), Jan. 25, 1988.
Betzig et al., "Collection Mode Near-Field Scanning Optical Microscopy", *Appl. Phys. Lett.*, 51 (25), Dec. 21, 1987.

*Primary Examiner*—Bruce C. Anderson
*Attorney, Agent, or Firm*—Townsend and Townsend

[57] ABSTRACT

A point projection photoelectron microscope is disclosed. A specimen is enclosed in a photoconductor that is subject to the photoelectric effect. The specimen is positioned on a pedestal in an evacuated chamber. The specimen is bombarded by radiation, either of light, ultraviolet radiation, or soft x-rays. The is in a vacuum chamber and it is highly charged with a negative potential. The vacuum chamber includes a surface sensitive to electron flow for making an image. This surface is a phosphor screen or an image intensifier having the capability to be gated for imaging or not imaging incident electrons or a segmented electron collecting anode for electronic imaging. In operation, a collimated beam of radiation, ranging from light to soft x-rays is projected through a specimen disposed in the photoemitter. An image of the specimen is produced on the photoemitter. The light or x-ray which impact on the photoemitter which produce electrons by the photoelectric effect. The electrons migrate beyond the photoemitter where the electric field at the tip of the photoconductor radially repels the electrons to and towards the imaging surface, typically the image intensifier.

21 Claims, 4 Drawing Sheets

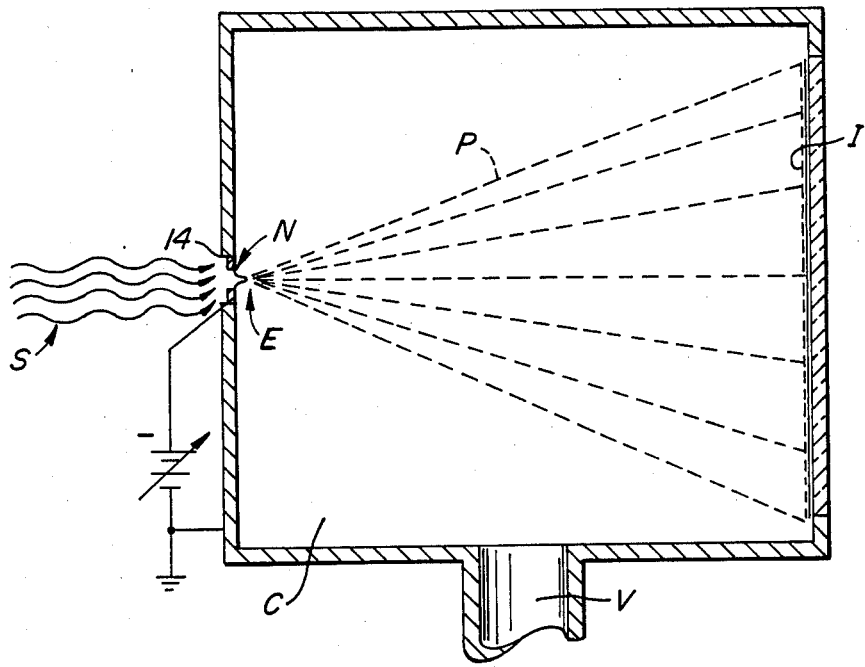
FIG._1.
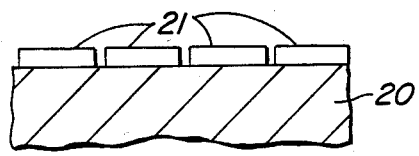
FIG._3A. PRIOR ART
FIG._3B. PRIOR ART
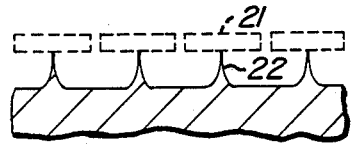
FIG._3C.
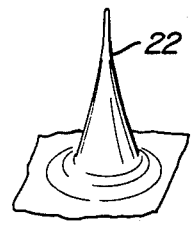
FIG._3D.

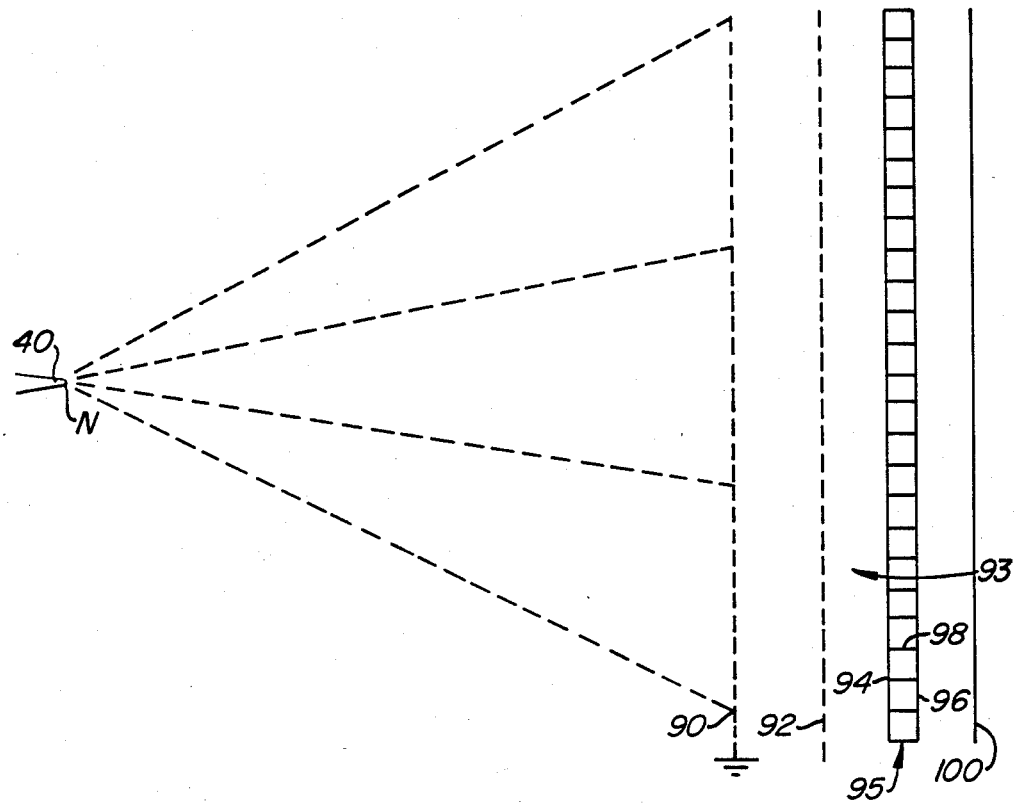
FIG._2.

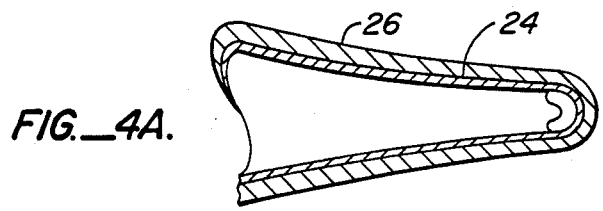
FIG._4A.
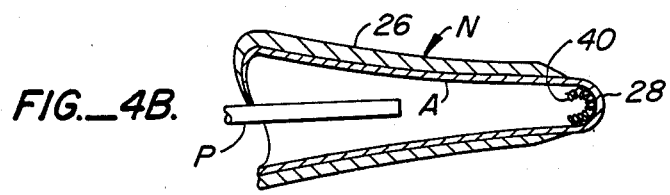
FIG._4B.
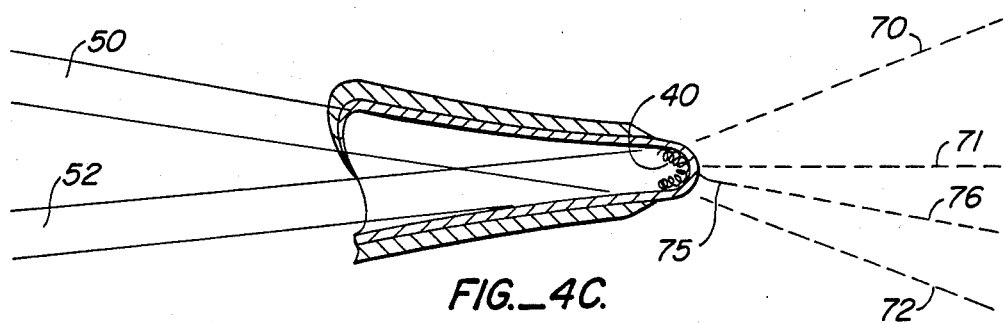
FIG._4C.
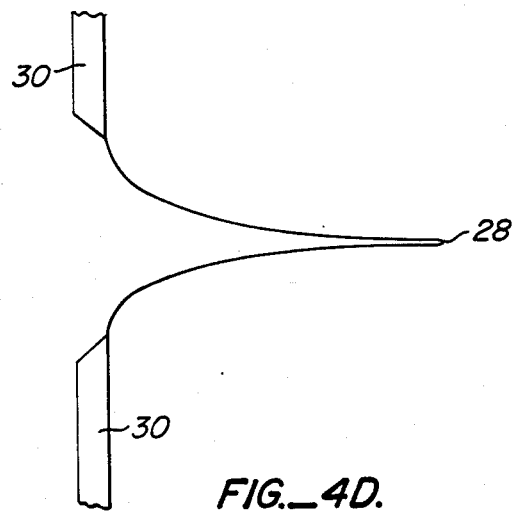
FIG._4D.

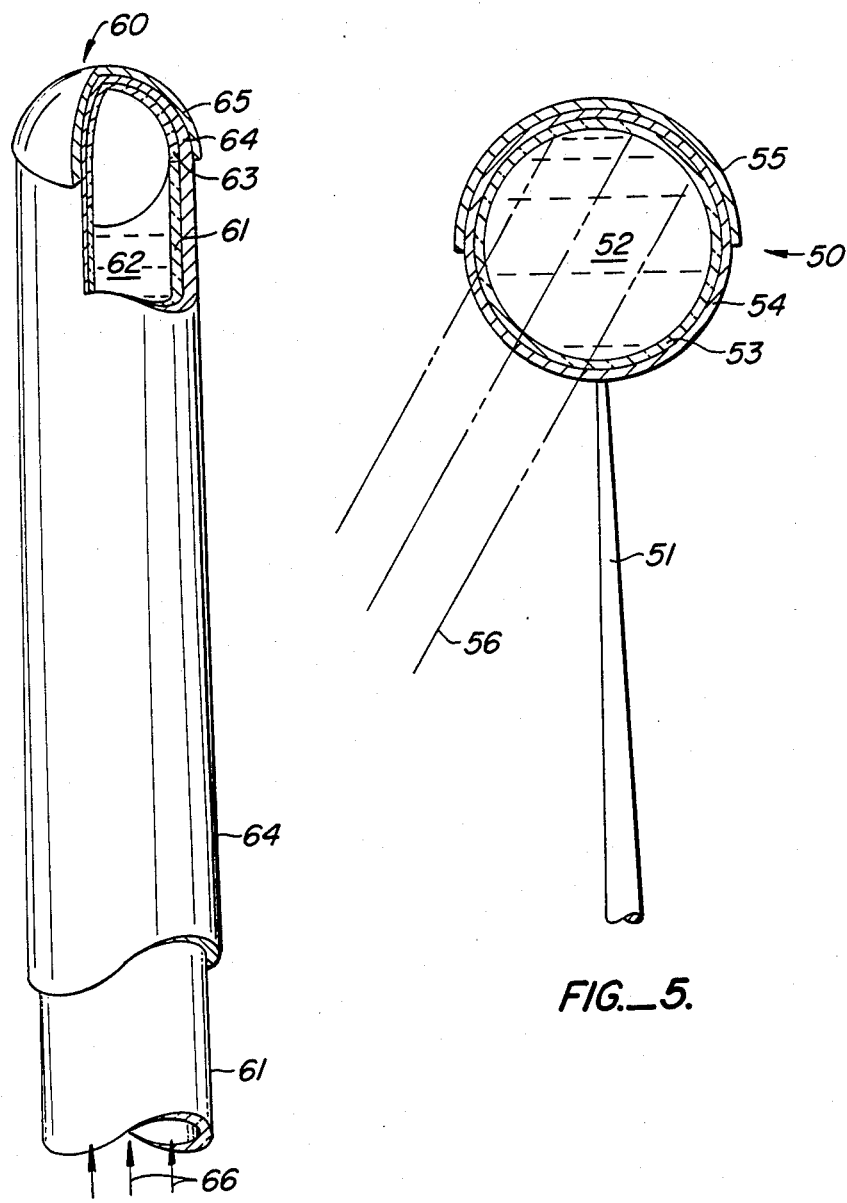
FIG._5.
FIG._6.

POINT PROJECTION PHOTOELECTRON MICROSCOPE WITH HOLLOW NEEDLE

This is a continuation-in-part of application Ser. No. 906,354, filed on Sept. 11, 1986. Abandoned

FIELD OF THE INVENTION

The present invention relates to microscopes. More particularly, the invention relates to microscopes which generate images by passing x-rays or other electromagnetic radiation through a sample.

BACKGROUND AND PRIOR ART

Contact microscopy is known. Typically, x-rays are directed onto a sample placed on an x-ray sensitive medium. The x-rays may be continuous or pulsed with nanosecond duration and high intensity and are recorded on the medium. Thereafter, the medium is developed and the x-ray shadow image is examined with an electron microscope. Excellent image contrast results. See Synchrontron Radiation published by Plenum Press of New York, N.Y. 1980, pp. 277-322.

No continuous imaging for observing specimens in vivo is usually possible. A single picture of the specimen is all that is provided. Stereoscopic imaging with depth information is also not easily obtained as specimen must be lifted off medium and redeposited on new medium for multiple exposures.

It is also known to construct a photoelectron x-ray microscope on a flat surface. X-rays bombard the flat surface through a sample and thereafter liberate electrons from a semitransparent photocathode. This contact method of producing an electron image requires electron optics to image the electrons. These optics are expensive and complex.

Point source x-ray projection microscopes are known. A point source of x-rays projects an enlarged shadow of a sample onto a distant image plane. This method has limitations in that image resolution is lost due to finite x-ray source size—a point source is never truly produced. Further there is a need to have the object very close to the x-ray source, which is a practical limitation.

Field ion and field emission microscopy is known. The sample is the tip of a very sharp needle. A high electric field is generated at the needle point causing electrons or ions to flow radially from the needle to a distant screen producing an enlarged image. High magnification with 2 to 3 Å resolution in the ion case results. See Field Ion Microscopy published by AMERICAN ELSEVIER 1969. Unfortunately using this technique, there has been little success in examining biological samples placed on the surface of the needle. Images of atomic structure on the exterior surface of the needle can only be produced. Since the needle must be exposed to a vacuum, in vivo examination of the specimen is again not possible even if the other problems were solvable.

Scanning x-ray microscopes are known. In such technique a collimated x-ray beam is scanned in a raster pattern. An image is created by mapping the point to point intensity of the transmitted beam. Unfortunately, in this technique, the limitations include the size of the beam that one is able to produce. Consequently, the resolution of the image is limited to the beam diameter.

Microscopes using focusing elements for x-rays are known. These use grazing incidence optics or zone plate focusing techniques on the x-rays. Unfortunately in such microscopes, the x-rays are poorly focused by presently available optics.

Electron microscopes are known. In such microscopes samples are cut to extremely thin sections. Unfortunately, the contrast of such thin section material when bombarded by electrons is not good. Therefore, stains are frequently required in use. Moreover, the sample is placed in a vacuum chamber for observation. Therefore, in vivo observation of the sample is not possible.

SUMMARY OF THE INVENTION

A point projection photoelectron microscope is desclosed. A specimen is enclosed in a photoemitter that is subject to the photoelectric effect. The specimen is positioned on a pedestal in an evacuated chamber. The specimen is bombarded by radiation, either of light, ultraviolet radiation, or soft x-rays. The photoemitter is in a vacuum chamber and it is highly charged with a negative potential. The vacuum chamber includes a surface sensitive to electron flow for making an image. This surface is a phosphor screen or an image intensifier having the capability to be gated for imaging or not imaging incident electrons or a segmented electron collecting anode for electronic imaging. In operation, a collimated beam of radiation, ranging from light to soft x-rays is projected through a specimen disposed in the photoemitter. An image of the specimen is produced on the photoemitter. The light or x-ray which impact on the photoemitter which produce electrons by the photoelectric effect. The electrons migrate beyond the photoemitter where the electric field at the tip of the photoemitter radially repels the electrons to and towards the imaging surface, typically the image intensifier. The irradiating source (light or soft x-ray) can be pulsed and the image intensifier time gated with respect to the pulse so that electrons having a relatively slow initial velocity, which implies little transverse momentum, are used for the production of the image. There results an image having high magnification which produces high resolution of a sample in vivo. It will be noted the magnification is approximately the distance from tip of a needle to the screen divided by the radius of the needle tip. Resolution in order of 100 Å are possible. It is important to note that magnification is produced without the use of a lens.

OTHER OBJECTS AND ADVANTAGES

An object of this invention is to disclose a photoelectric effect microscope for producing an electron image of a sample placed on the inside of a hollow needle. The hollow needle is constructed of material sufficient to produce from irradiation (selected to range from optical wavelengths to soft x-ray wavelengths) electrons via the photoelectric effect. The specimen is positioned on a pedestal in an evacuated chamber. The needle is communicated to atmosphere on the interior and to a vacuum on the exterior and electrified negatively. Collimated radiation bombarding a sample on the inside of the needle, produces a contact image on the end of a needle, which contact image produces electrons. The electrons are accelerated by the electric field radially away from their point of image on the end of the needle to an image plane.

An advantage of this invention is that it can use either optical wavelengths or soft x-ray wavelengths. Superior contrast can be produced.

A further advantage of the disclosed technique is that the image produced at the end of the needle is essentially a contact image. Problems of focusing are held to a minimum.

Yet another advantage of this invention is that the magnification required is produced by the radial acceleration of the electrons. The needle for its own part provides the necessary optical element when electrified. Extensive electron optics, grazing incidence optics and refractive or reflective optics are all avoided.

A further advantage of the optic and x-ray irradiation is that these can be tuned to the particular element that an observer wishes to view from a sample. For example, by selecting soft x-ray radiation just above an absorption edge— say the absorption edge for carbon in a sample— the carbon will be emphasized in the image of the sample.

Yet an additional advantage is that the x-rays can be continuously pulsed in recording movement of a sample in vivo. Sequential observations of a specimen are possible before significant damage to the specimen occurs due to the effects of the incident radiation.

Yet another advantage of this invention is that the sample is placed near an extremely high electric field environment. Since, however, the conducting needle in effect surrounds the sample, the sample is not effected by the field. The electron image, however, is produced as a direct result of electrons accelerating away in the surrounding electric field. Due to the strength of the field, an image nearly free of chromatic aberration can be produced. Also, due to the high electric field, space charge effects are minimized.

Yet another advantage of the disclosed technique is that stereo images are possible. Simply stated, by impacting the sample at the end of the needle with collimated rays of varying angularity, stereo images can be projected. Thus, three dimensional information is available utilizing the technique of this invention.

A further advantage is that the x-rays can be adjusted in intensity. They can be held and pulsed at a level where destruction of life or structure within the specimen is delayed. Although the resolution will suffer at lower intensities, this delay can in effect enable the specimen to be observed in vivo. This in vivo observation can occur before any substantial effect on the specimen occurs due to radiation damage. Alternately, one can use a very intense short burst of radiation which will give a very high resolution image. This high resolution image is due to the fact that the specimen remains intact long enough for the image to be recorded before the specimen disintegrates.

A further object of this invention is to disclose an apparatus and method for the focus of the produced electron image. According to this aspect, the sample on the inside of the beam receives pulsed bursts of radiation. The pulsed bursts of radiation produce electrons having variant amounts of momentum as they leave the photocathode on the end of the needle to the area of high electric field. The electrons are radially accelerated in the vacuum chamber to an image collection point, preferably a gated image intensifier. By having the image intensifier gated at precise time intervals with respect to the interrogating pulsed radiation, electrons having little initial momentum so as to produce only radial acceleration and a sharp image are received at the intensifier. All other electrons possessing larger momentums will arrive in a time domain which is outside of the gating of the intensifier. Thus, by the expedient of gating the intensifier relative to the pulsed image, high focus can be achieved.

A further object of this invention is to disclose a process of producing disposable needles for the disclosed microscope. A technique of photoetching of the needle for containment of the sample is disclosed. As a first step, a male needle member is produced by a photoetching technique known in the prior art. This male needle is thereafter coated with a material capable of producing photoelectrons when bombarded by interrogating radiation. Thereafter, the male needle member is etched away leaving the hollow needle which can receive samples, is disposable, and forms the electron optics of this invention.

Other objects, features and advantages of this invention will be more apparent after referring to the following specification and attached drawings in which:

BRIEF DESCRIPTION OF THE DRAWINGS

FIG. 1 is a schematic view of the x-ray microscope of this invention illustrating the needle confronted to a vacuum chamber illustrating in broken lines the path of radially accelerated electrons to an imaging surface;

FIG. 2 is a schematic cross section of an image intensifier having gating for discriminating out imaging electrons having a preferred velocity profile;

FIGS. 3A, 3B, 3C and 3D are examples of a prior art technique for fabricating a male needle;

FIGS. 4A, 4B, 4C and 4D illustrate sequentially the fabrication of the female and hollow needle, the placement of a sample within the needle, the irradiation of the needle to produce the desired image, and an overall view of a needle in section.

FIG. 5 is a drawing of a first alternative embodiment.

FIG. 6 is a drawing of a second alternative embodiment.

DETAILED DESCRIPTION OF THE PREFERRED EMBODIMENTS

Referring to FIG. 1, a vacuum chamber C has a needle N mounted to an opening 14. The needle is hollow, has its inside exposed to atmosphere exterior of chamber C and its outside exposed to the interior of the chamber C. A vacuum is drawn on the chamber in the range of pressure less than or equal to $10^{-6}$ torr through pumping line V. Thereafter, a radiation source S irradiates the inside of the needle producing in the needle material electrons by the photoelectric effect.

The reader will understand that minimum vacuum is required to permit electron flow. Generally a vacuum of at least $10^{-2}$ torr must be drawn. Higher vacuum is desired to minimize sputtering damage to needle.

The end of the needle N creates a high electric field when charged. The high negative electric field causes electrons produced by the photoelectric effect to undergo rapid, radial acceleration. The produced electrons generally follow a path P to an image surface I. Image surface I can be a phosphor screen, an image intensifier capable of being gated or a segmented electron collecting anode for electronic imaging. At the image plane I, the contact image of the sample on the material at the point of the needle is produced. A magnified overall image results.

I would like to point out that a contact image is also a special example of an extreme near field Gabor hologram. See Synchrontron Radiation Research reference, Sec. 3.1.3, page 293 published by Plenum Press. Therefore, this invention may be useful for holography in addition to the simple contact shadowgraph image. Holography has the important advantage of not having the resolution fall off as the specimen detail to photocathode distance is increased. In the x-ray wavelength band, this could give less than 100 Å resolution throughout a fixed specimen in vivo.

Having summarized this invention, the detailed parameters will now be set forth. First, and with respect to FIGS. 3A-D and 4A-C, the construction of the needle, placement of the sample and imaging of the sample will be discussed. Secondly, the operating parameters of the microscope will be set forth.

Referring to FIG. 3A, a technique is illustrated for needle fabrication. Originally, this technique was designed for fabrication of large area field emission arrays. See article entitled Etching Procedure Fabrication of Large Area Field Emission Arrays by R.N. Thomas, R.A. Wickstrom, D.K. Schroder and H.C. Nathanon, Westinghouse Research Laboratories, Pittsburg, Pa. published in Solid State Electronics 1974, Vol. 17 pp 155-163, printed by the Pergamon Press of Great Britain. In this article, it is disclosed that an etchable substrate 20 is covered with etched maskings 21 in a circular format. When exposed to etching materials, the etchant undercuts the masking 21 as illustrated in FIG. 3B to a needle format as illustrated in FIG. 3C. A needle 22 results.

Needle 22 can be controlled as to the radius of curvature and diameter at the needle end by various techniques mentioned in the article. As the needle in FIG. 3D was utilized for large area field emission arrays, the further processing illustrated with respect to FIGS. 4A-4C, comprises my invention and has no connection with the prior art. In short, the prior art does not disclose my concept of making the needle hollow. There are other ways to produce similar structures but this appears to be the most convenient.

Referring to FIG. 4A, needle 22 has been coated with a thin material 24 and a thicker reinforcing material 26 and the original needle 22 etched completely away leaving only the coatings 24 and 26. Coating 24 is a material subject to the photoelectric effect.

Referring to FIG. 4B, the needle is illustrated having a protective and reinforcing coating 26 deposited over the coating. This material serves to reinforce the needle against the physical pressure forces of the atmosphere on one side, to and towards the evacuated portion of the chamber on the other side. As can be seen, coating 26 stops adjacent the point of the needle at 28. This can be accomplished by a masking and etching step.

The reader should appreciate that it is not necessary for the photocathode to have a radius of curvature equivalent to twice its diameter (in other words to be a hemisphere). Even a flat photocathode forming the tip closure of a hollow needle (basically a truncated needle) will form a radially projective electron image. The image will have some distortion which may be acceptable. By simply undercutting the mask 21 and stopping at a desired tip diameter before undercutting is complete, one will form a flat photocathode after coating and etching out of the needle 22. Forming a radius of curvature on tip can be accomplished by chemical etching or thermal blunting of the needle 22 before it is coated and etched out.

Stopping here the specific mechanics of the needle and its desired properties can be discussed. The thickness of the coating is small. A 1,000 Å thickness of a material subject to the photoelectric field at 28 will be sufficient. The coating should be thick enough to stop the radiation but not so thick as to not transmit the photoelectrons. In other words, it is a semitransparent type photocathode. Reinforcing layer 26 is typically constructed of a metal film several microns thick. Dielectric, semiconductor, or polymer films are also possible. Regarding the material of coating 24, any material subject to the photoelectric effect will suffice. Gold, for example, is a desirable substance. Special low work function coatings are necessary to work in the optical wavelengths. Photocathodes incorporating non-metals such as cesium iodide are also useful due to their high quantum yield and low average photoelectron energy.

The area of the end of the needle is small. Therefore an extremely thin coating will suffice as the required barrier against the atmospheric and electrostatic force at the end of the needle. The elctrostatic force is in fact equivalent to over ten atmospheres under standard operating conditions.

I prefer iridium for the coating 24 from which the needle is made. This is because iridium is very inert to most chemicals, has high strength and should be optimally employable in the disposable needle set forth. Other hard noble metals are possible.

The needle is provided with a flange 30. (See FIG. 4D.) Flange 30 is the surface upon which the needle rests in aperture 14 in the vacuum chamber C. This flange 30 is left over substrate which was masked so as to not be etched away.

The reader will note that the needle is extremely small. For instance, a needle point radius of the order of 1-5 microns is typical.

Having discussed the fabrication of the needle and continuing at FIG. 4B, the placement of the sample and the irradiation of the sample may now be set forth.

Referring further to FIG. 4B, a pipette P of the drawn glass fiber type is illustrated. The pipette deposits a sample 40 at the inside of the needle structure N. It is this sample 40 which when irradiated by interrogating radiation produces a contact image on the material 28 of the needle.

Referring to FIG. 4C, collimated radiation 50 impinges upon the sample 40 immediately overlying the material 28 at the curved portion of the needle. The radiation is either optical or soft x-ray. For the purposes of this example, a soft x-ray image will be considered.

The material of the sample 40 attenuates the soft x-ray. It produces at the tip of the needle an essentially contact image. The contact image is produced by the x-rays in the material subject to the photoelectric effect and therefore produces electrons. The electrons produced are proportional in intensity to the transmitted image of the irradiated specimen.

The reader will understand that a contact image of the sample 40 is in effect produced. That is to say, the sample has a very small spatial depth overlying the end point of the needle. This small spatial depth minimizes penumberal blurring of the image. That is to say, the radiation produced image does not have the shadow of its details blurred because of the appearance of the radiation coming from a source having a discrete radiating diameter. The main source of blurring will be due to diffraction.

As also shown in FIG. 4C, it is possible to irradiated the sample 40 from two angles with respect to the needle. In FIG. 4C two beams of radiation 50, 52 are illustrated. These are preferably alternately irradiated on the target to produce alternate, sequential, and closely temporally spaced images. Separate images may be recorded on separate cameras using fast electro-optic shutters to avoid image superposition. Naturally, a fast decay phosphor is necessary on the imaging screen to avoid a persistent image from the first image being superimposed on the second. Alternatively a segmented anode with fast electronics can record the multiple exposures.

I prefer to pulse the radiation from source S shown in FIG. 1. It is possible when pulsing the image from source S to avoid blurring of electron image. In order that this aspect of the invention may be understood, I include herewith first an explanation of the source of the blurring and thereafter, the preferred use of an image intensifier to gate the receipt of the image with respect to the pulse to improve focus.

Referring to FIG. 4C, it will be appreciated that electrons created by the photoelectric effect be accelerated away from the point 28.

The electrons will radially accelerate away from the needle point along path lines 70, 71, and 72. Presuming the path of the electrons is radial, the electrons will carry information about a contact image at the end point of the needle.

Unfortunately, electrons produced by the photoelectric effect do not have the same velocity and direction from their point of production. Some electrons are fast and initially travel in a direction which is other than radial, due to a transverse component of initial momentum when originally liberated by the photoelectric effect. Other electrons are slow. In either event, the produced image can become blurred. This spread in energy can be minimized with a coating of a material such as cesium iodide.

I have illustrated the non-radial path of such a fast electron at 75. The electron path 75 is that of a relatively fast moving electron moving out at an angle which is other than radial with respect to the point of the needle 28. The electrons initial momentum causes its trajectory to occur along the path 76.

The reader will remember that the image produced at the end point of the needle 28 is a contact image. Being a contact image, if an electron moving along the path 76 is allowed to impinge at the image plane I, an undesirable blurring of the image can occur.

Fortunately, an image intensifier I imparts the ability to gate or select the time interval of electrons received at the image intensifier I. Naturally, I gate the time interval to receive the radially moving electrons along the paths 70, 71, 72 and discriminate out shorter time interval electrons such as that illustrated in path 75 from producing an image I.

Referring to FIG. 2, I illustrate a specimen 40 within a needle N. Collimated radiation 50 impinges upon sample 40, and thereafter produces electrons in needle N having the image information. The local electric field about the point of the needle produces all the acceleration to the produced electrons — they are radially accelerated away.

The electrons are accelerated by the negative potential of the needle. The needle thus produces the only force of acceleration; image information is preserved.

It will be understood that the photoelectric effect produces electrons having varying velocities. For example, the velocities of electrons leaving the needle can vary in the range of 30 EV. It will be further understood that moving electrons can have velocity vectors that degrade the image information acquired at the sample. Therefore, it is preferred to have electrons ultimately imaged which have as little as possible relative velocity with respect to the sample when the electrons are originally generated by the photoelectric effect.

Thus, when the acceleration from the electric potential at the end of the needle occurs, the velocity attained will be due to the acceleration force provided by the potential of the negative field at the end of the needle and residual (and undesired) velocity from the producing photoelectric effect itself.

Some exemplary voltages will help. Assuming the tip of the needle is at a voltage of $-10,000$ volts, electrons will be accelerated away from the needle and reach energies of 10,000 to 10,030 EV.

No forces of acceleration other than that provided by the needle should be provided to the electrons until they reach the area where imaging will occur. This being the case, the electrons will see a grounded screen 90. This screen has the effect of shielding the electrons from any extraneous forces that will either degrade the image information or effect the desired radial acceleration that produces the desired magnification.

At this juncture, it will be seen that the electrons having low energy (about 10,000 EV) are desired; the electrons having higher energy (about 10,030 EV) are not desired. The remainder of the illustrated imaging circuitry effects this discrimination.

Specifically, a second retarding potential screen 92 is provided. This screen has a negative voltage slightly less than the needle voltage— in the order of $-9,990$ volts for the given example. Thus, the electrons will be decelerated by the screen to energies in the range of 10 EV to 40 EV for the illustrative voltages used here.

After passage through the screen 92 with resultant deceleration, the electrons will enter drift area 93 between screen 92 and a microchannel image intensifier plate 95. Plate 95 includes a front surface 94, a series of conventional microchannels for electron avalanche image intensifying and a rear surface 96 which can have its potential made less negative than front surface 94 for promoting the electron avalanche.

It will be appreciated that the electrons in the drift area 93 will be temporally classified according to energy with the fast (and undesired) electrons traversing drift space 93 first and the slower (and more desired) electrons traversing the drift space 93 second. This being the case, surface 96 is maintained at the same potential as surface 94 to avoid image intensification of fast electrons during their time period of arrival at surface 96. Thus, during this time period surface 96 will be maintained at $-9,990$ volts, the same voltage as decelerating screen 92 and surface 94.

When the slow moving electrons reach surface 94— having 10 EV—the rear surface 96 is switched by conventional circuitry to a voltage closer to ground $-9000$ volts in the example given. Therefore, multiplication of the electrons in the microchannel plates will occur which have the slower velocity only.

Thereafter, the imaging is conventional. Microchannel plate then produces the intensified electron image. Phosphor screen 100, at a potential closer to ground produces the image.

The reader will realize that the image intensifier I can be replaced by a phosphor screen for the regular imaging of the electrons. In addition, one can use a simple phosphor screen and do time domain selection of the electrons which contribute to the image by the camera recording device with a fast electro-optic shutter. A very short persistence phosphor will then be required. A segmented anode is also usable for electronic imaging where the electrons arrival is recorded spatially by monitoring current.

The proceeding electron energy discrimination scheme requires the use of a pulsed radiation source and precise timing and switching electronics. One can operate this retarding potential energy discrimination arrangement in a different manner and use a continuous source of radiation. The higher energy electrons can be imaged by simply using the retarding potential to stop and repel the lower energy electrons. These electrons are not well imaged for high resolution; however, if one makes two different exposures, the desired result can be obtained. Specifically, one exposure is made without any retarding potential so that all the electrons are imaged. Next a retarding potential is used which is high enough to actually stop and repel the desired low energy electrons and a second exposure is made. To produce an image of the specimen utilizing just the low energy electrons, the difference in the two images is produced by subtracting the second image from the first. The difference between the two is simply the contribution of the low energy electrons. This subtraction can be done conveniently by computer image processing.

More sophisticated retarding potential energy discrimination schemes are known in the literature. The previous schemes are used as an example.

The imaging surface and screens associated with the imaging surface should be curved to keep the electric fields parallel to the electron trajectories, although they are shown flat in FIG. 2.

It will be understood where soft x-rays are utilized, a sharp image with under 100 Å resolution can be produced. Diffraction effects are limited due to the reduced wavelength. The degradation due to diffraction effects is reduced with respect to the optical wavelength light.

RESOLUTION $\simeq \lambda * \sqrt{D/\lambda}$ $\lambda$ = wavelength

D = distance from specimen detail to photocathode

For samples very close to photocathode, high resolution imaging is possible even with optical wavelengths (see references to "near field imaging"). These describe resolution of $\sim \lambda/20$.

It will be appreciated that I prefer to use pulsed x-rays. Continuous x-rays are not sufficiently intense to produce a high resolution image before radiation damage causes image degradation. Pulsed x-ray sources freeze the image so as to give an image of the specimen before radiation induced movement destroys the specimen. In other words, the specimen remains intact for the exposure time, even though it will be completely destroyed less than a millisecond later (pulse duration $\sim$ 10–100 nanosecond).

It is sufficient if the needle is irradiated by electromagnetic energy sufficient to generate the required photoelectric effect. Wavelengths between 3,000 Å and 1 Å are sufficient for the practice of this invention. By using soft x-rays with a wavelength between approximately 24 and 44 Å, high contrast in hydrated biological specimens can be obtained. This is because water is relatively transparent compared to carbon in this range. By utilizing special coatings (which cannot be exposed to air) wavelength can be extended to $\sim$ 6000 Å.

These coatings can be deposited in the microscope after pump down or the needle can have a protective cap which keeps the surface in an inert atmosphere when it is exposed to air. The reason to go to these long wavelengths is to completely avoid radiation damage. The resolution will of course suffer, although details right adjacent to the photocathode surface may be very well resolved as they are imaged in the near field regimen.

Various alternative embodiments of the invention are possible without departing from the basic spirit, idea and scope of the invention. Two such alternative embodiments are shown in FIGS. 5 and 6.

Both of the embodiments shown in FIGS. 5 and 6 eliminate the need to fabricate a needle or pedestal in accordance with the technique described with reference to FIG. 3. Otherwise, these embodiments operate in the same manner as does the previously described embodiment. Both embodiments have a sample mounted on a pedestal.

The embodiment shown in FIG. 5 utilizes a microencapsulation technique which is well known in the art. For example, an article in the Journal of Applied Physics, Vol. 47, No. 2, February 1976, p. 741 entitled "New Wet-Replication Technique-Replication of Water Droplets" by S. Basu, G. Hausner and D.F. Parsons describes a technique for encapsulating tiny droplets of water. Many of the samples which one would like to examine utilizing the present invention contain a large percentage of water. These specimens can be encapsulated utilizing the previously know microencapsulation techniques and examined as described below. It should be appreciated that there are many known microencapsulated techniques.

FIG. 5 shows a microcapsule 50 which contains a specimen 52 mounted on a needle 51. The needle shown in FIG. 5 is an alternative to the needle N shown in FIG. 4. X-rays are passed through the specimen 52 along path 56. The x-rays in path 56 pass through a conventional window in chamber C (the window is conventional and it is not specifically shown).

The specimen 52 is microencapsulated with a layer 53 of silicon monoxide using the techniques described in the previously referenced article. The microcapsule is then mounted on needle 51 by merely bringing the needle into contact with microcapsule. Alternatively, the specimen 52 may be microencapsulated after it is placed on the needle 51. Normal forces will hold the microcapsule to the needle. After it is mounted on the needle 51, the microcapsule 50 is sputter coated with a layer of conductive material 54 which could, for example, be a metal such as gold. This layer functions as a adhesion layer to hold the microcapsule to the needle as well as a photocathode. While not necessary in order to enhance the operation of the device, an additional layer 55 of photoemitter such as cesium iodide can be deposited on one-half of the microsphere.

The layer of metal 54 which is deposited on the entire sphere can be deposited using sputtering techniques where the material being deposited has the ability to surround the entire object. The partial layer 55 of cesium iodide can be deposited by vapor evaporation techniques which are very directional in nature and hence a sample put in such a device would only coat one side of an object thus forming a semicircular layer 55.

A mounting bracket (not shown) positions needle 51 in the vacuum chamber C at the position of needle N in FIG. 1. Needle 51 would be inserted into the chamber C using a conventional vacuum seal.

Electrons generated on photo emissive layer 55 are imaged in exactly the same manner as that described for the first embodiment. While in this embodiment a needle 51 is shown, other types of long narrow pedestals could be used.

A second alternate embodiment 60 of the invention is shown in FIG. 6. In this embodiment of the invention, a small amount of the specimen is pulled into a pipette 61 in a conventional manner. This small amount of the specimen fills the bottom portion 62 of the pipette 61. In this embodiment the pipette serves as a pedestal.

After the specimen is placed in the pipette 61, the bottom portion of the pipette is coated with a layer of silicon monoxide 63 using the same previously referenced technique used to coat microdroplets of water. Layer 63 is shown as only coating the bottom of the pipette 61. In practice, the coating may extend over the walls of the pipette 61. Such extension of the coating layer 63 has no practical effect on the operation of the device since layer 63 is covered by a conductive layer 64.

Three layers 63, 64 and 65 are formed in the end of the pipette 61, these layers correspond to layers 53, 54 and 55 shown in FIG. 5. In the embodiment shown in FIG. 6, the x-rays are directed into the specimen 62 along a path 66 which proceeds through the center of the pipette.

The pipette shown in FIG. 6 has straight walls. A fine glass capillary drawn to the desired size would be one way to produce the initial pipette. For the purpose of this invention, it is not necessary for the walls to be straight. The walls could taper down from a larger size as does the hollow needle shown in FIG. 4. The only conceptual difference between the pipette shown in FIG. 6 and the hollow needle of FIG. 4 is that the specimen end of the hollow needle of FIG. 4 is initially closed while the pipette is initially open. For the purpose of this invention, we define a pipette as any structure of the form of a tube with either straight or tapered walls with an open end for depositing a specimen.

If the material of the pipette is non-wetting, a single droplet may be conveniently placed on the end of the pipette without the droplet being drawn into the pipette by surface tension forces. This situation is optimal for forming a hemispherical photocathode on the end of the pipette.

Using the embodiment shown in FIG. 6, the specimen is inserted into the vacuum chamber shown in FIG. 1 and mounted by a bracket (not shown) at the same position as needle N. The amount of magnification is determined by the distance from the photoconversion layer to the image means. The photoconversion means should be small relative to the size of the vacuum chamber C so that the electrons will travel substantially radially. A ratio larger than one thousand to one is satisfactory. A ratio larger than ten thousand to one is preferred.

It is noted that the techniques for sealing elements in a vacuum chamber are well known in the prior art and will not be described in detail herein.

Additional improvements in the operation of the device can be achieved by cooling the specimen below the freezing point so that there is a diminished movement of the specimen. Radiation damage distortion of the specimen can be reduced by this technique.

A still further alternative embodiment of the invention can be made by using a dielectric coating that liberates electrons which are temporarily trapped in the coating in the absence of an applied voltage. The trapped electrons can later be extracted, by applying the needle voltage, and imaged. It is noted that the previously described embodiments use photoelectrons that are promptly emitted from the coating at the time of exposure to form the image. This embodiment uses electrons that are trapped to later form an image. A material which exhibits this effect is an alkali halide coating with the electrons trapped in color centers. The advantage of this embodiment is that the trapped electrons would have little initial kinetic energy when they are extracted and the image would therefore be sharper.

The above-described and other changes in form and detail may be made without departing from the spirit and scope of the invention as defined by the following claims.

What is claimed is:

1. A microscope comprising:
   an evacuated chamber having walls;
   a pedestal situated on one side of said chamber for holding a specimen;
   a photoconversion means surrounding at least one side of said specimen a first surface of said photoconversion means being exposed to said evacuated chamber;
   means directing radiation through said specimen to said photoconversion means whereby said photoconversion means generates electrons on said first surface in a pattern representing characteristics of said specimen;
   an imaging surface for producing an image in response to charges which are incident thereon, said imaging surface being located in said evacuated chamber, remote from said photoconversion means, and on the opposite side of said photoconversion means from said pedestal;
   means for creating an electrical potential between said photoconversion means and said walls whereby charges released by said photoconversion means are substantially radially accelerated from said photoconversion means towards said imaging means and whereby an image of said specimen is generated on said imaging means.

2. A microscope comprising:
   a hollow needle having an opening adjacent one end, a closure adjacent the other end and made from a material which produces a photoelectron response to incident radiation;
   said hollow needle defining a site within said needle for receiving a sample on the inside of the needle adjacent the closure;
   a chamber for receiving the needle at one portion and having a second portion for receiving and recording an electron image, said chamber configured for communication to a vacuum pump to permit a vacuum to be drawn within said chamber;
   means for applying a negative charge to the needle to cause electrons to move from the needle to the image recording surface;
   means for impacting said sample with radiation sufficient to produce in said needle photoelectrons whereby the radiation is attenuated with a contact image of the sample, the radiation impacts the closed end of said needle to produce photoelectrons and said photoelectrons are radially accelerated away from said needle to produce an electron image of said sample at the tip of said needle magnified by said radial acceleration; and means for recording an electron image from said photoelectrons.

3. The invention of claim 2 and wherein said means for impacting said sample with radiation includes pulsed radiation.

4. The invention of claim 2 and wherein said means for impacting said sample with radiation includes soft x-rays.

5. The invention of claim 2 and wherein said second portion of said chamber for receiving and recording an image includes an image intensifier.

6. A process of microscopy including the steps of:

providing a hollow needle having an opening adjacent one end, a closure adjacent the other end and defining a site for receiving a sample on the inside of said needle adjacent said closure, said provided needle closure made from a material which produces electrons responsive to incident radiation;

placing a sample in said needle at said site for receiving said sample;

providing a chamber having a vacuum;

mounting said needle to said chamber to expose the hollow portion of said needle to atmosphere and the pointed portion of said needle to the interior of said chamber;

drawing a vacuum on said chamber;

applying a negative charge to the needle;

providing an image recording surface on the interior of said chamber;

impacting said sample with radiation sufficient to produce electrons at the closed end of said needle whereby the radiation is attenuated with a contact image of the sample, said attenuated radiation impacts said closed end of said needle to produce photoelectrons via the photoelectric effect and said photoelectrons are radially accelerated away from said needle to produce an electron image of said radiation at said image surface; and recording said image at said image recording surface.

7. The process of claim 6 and wherein said impacting step includes the step of pulsing said radiation.

8. The process of claim 6 and wherein said drawing a vacuum step includes a vacuum in the range of $10^{-2}$ and $10^{-6}$ torr.

9. The process of claim 6 and including the additional step of discriminating out slower moving electrons from said needle whereby electrons having slow velocities of initial photoelectric production will be imaged.

10. The process of claim 6 and wherein said impacting step includes impacting said sample with optical wavelength radiation.

11. The process of claim 6 and wherein said impacting step includes impacting said sample with soft x-ray radiation immediately above an absorption edge of atoms in said sample.

12. The invention of claim 6 and wherein said placing and sample step includes placing a living sample.

13. In a microscope of the type wherein radiation impinges through a sample onto a photoelectric media which produces photoelectrons responsive to said radiation and said photoelectrons are accelerated away from said media by an electric potential to and towards a surface having means for recording an image from said photoelectrons, the improvement in said microscope comprising:

a hollow needle having an open end, a closure adjacent the other end, made from material which produces photoelectrons responsive to incident radiation;

a site within said needle adjacent the closure of said hollow needle for receiving a sample on the inside of the needle adjacent said closure whereby radiation incident on the inside of said needle produces electrons on the outside of said needle for acceleration to and towards said image recording surface.

14. The invention of claim 13 and wherein said needle includes a surface thick enough to stop bombarding x-rays but thin enough to transmit photoelectric effect generated electrons.

15. The invention of claim 13 and wherein the tip of said needle is iridium.

16. The invention of claim 13 and wherein the tip of said needle has a radius of curvature in the range of 10 to 50 microns and the diameter of said needle is in the range of 1 to 20 microns 17. In a photoemission microscope including a chamber having a vacuum, a wall of said chamber for receiving and recording an electron image, a site for discharging photoelectrons having a negative charge applied thereto; and means for irradiating a sample with radiation, the improvement comprising:

a hollow needle having an opening adjacent one end, a closure adjacent the other end, said closure made from materials which produce photoelectrons responsive to said incident radiation;

said closure of said said hollow needle defining a site for receiving a sample on the inside of said needle adjacent the closure whereby radiation on the inside of said needle defines a contact electron image on said closure and projects said image to said chamber sidewalls.

18. The invention of claim 17 and wherein said closure is made from a class of materials subject to the photoelectric effect including metals, semiconductors, or dielectrics.

19. The invention of claim 17 and wherein said closure is made from iridium.

20. The invention of claim 17 and wherein portions of said needle are reinforced with materials sufficient to maintain said needle from rupture across atmospheric pressure.

21. The process of claim 6, and wherein said impacting step include coherent radiation and said recording step includes the step of recording a holographic image.

22. A microscope comprising:

a needle like support having a specimen adjacent one end, a coating on said specimen made from a material which produces photoelectrons responsive to incident radiation;

a chamber for receiving said needle-like support at one portion and having a second portion for receiving and recording an electron image, said chamber configured for communication to a vacuum pump to permit a vacuum to be drawn within said chamber;

means for applying a negative charge to the needle-like support to cause electrons to move from the needle to the image recording surface;

means for impacting said sample with radiation sufficient to produce in said needle-like support photoelectrons whereby the radiation is attenuated with a contact image of the sample, the radiation impacts said coating to produce photoelectrons and said photoelectrons are radially accelerated away from said needle to produce an electron image of said sample at the tip of said needle-like support magnified by said radial acceleration; and means for recording an electronic image from said photoelectrons.

23. A microscope adapted to examine a microencapsulated specimen, said specimen being coated on at least one side with material subject to the photoelectric effect, comprising:

an evacuated chamber;

means positioning at least said first one side of said specimen in said evacuated chamber;

means directing radiation through said specimen to said material subject to the photoelectric effect whereby said material generates electrons on said first surface in a pattern representing characteristics of said specimen;

an imaging surface for producing an image in response to charges which are incident thereon, said imaging surface being located in said evacuated chamber; and means for creating an electrical potential between said material subject to the photoelectric effect and said imaging means whereby charges released by said material are radially accelerated from said material towards said imaging means and whereby an image of said specimen is generated on said imaging means.

24. A microscope for examining a specimen held in a pipette which has an open end, said open end being coated with a material subject to the photoelectric effect, comprising:

an evacuated chamber;

means holding said end of said pipette with said sample in said evacuated chamber;

means directing a beam of energy through said pipette to said specimen whereby said material subject to the photoelectric effect generates electrons on said first surface in a pattern representing characteristics of said specimen;

an imaging surface for producing an image in response to charges which are incident thereon, said imaging surface being located in said evacuated chamber, means for creating an electrical potential between said material subject to the photoelectric effect and said imaging means whereby charges released by said material are radially accelerated from said material towards said imaging means and whereby an image of said specimen is generated on said imaging means.

25. The invention of claim 1 wherein the electrons generated by said photoconversion means are temporarily stored in said photoconversion means prior to being imaged.

26. The invention in claim 22 wherein the specimen is at a low temperature.

* * * * *